United States Patent [19]
Sarkisian et al.

[11] Patent Number: 5,370,700
[45] Date of Patent: Dec. 6, 1994

[54] PROSTHETIC KNEE JOINT

[76] Inventors: James S. Sarkisian, 8415 Grant St., La Mesa, Calif. 92035; Clarence F. Batchelder, 17087 Skyline Truck Trail, Jamul, Calif. 92035-9712

[21] Appl. No.: 19,216

[22] Filed: Feb. 19, 1993

[51] Int. Cl.$^5$ .............................. A61F 2/38
[52] U.S. Cl. .............................. 623/20; 623/18
[58] Field of Search .............. 623/20, 21, 18

[56] References Cited

U.S. PATENT DOCUMENTS

| | | | |
|---|---|---|---|
| 3,840,905 | 10/1974 | Deane | 623/20 |
| 4,007,494 | 2/1977 | Sauer . | |
| 4,224,699 | 10/1980 | Weber . | |
| 4,227,265 | 10/1980 | Frey . | |
| 4,229,841 | 10/1980 | Youm et al. . | |
| 4,242,759 | 1/1981 | White . | |
| 4,349,922 | 9/1982 | Agee . | |
| 4,352,212 | 10/1982 | Greene et al. . | |
| 4,598,992 | 11/1983 | Burstein et al. | 623/20 |
| 4,634,444 | 1/1987 | Noiles | 623/20 |
| 4,687,487 | 8/1987 | Hintermann | 623/18 |
| 4,769,039 | 9/1988 | Horber | 623/20 |
| 4,790,851 | 12/1988 | Suire et al. | 623/16 |
| 4,822,365 | 4/1989 | Walker et al. | 623/20 |
| 4,871,367 | 10/1989 | Christensen et al. | 623/20 |
| 4,944,758 | 7/1990 | Bekki et al. | 623/21 |
| 4,963,153 | 10/1990 | Noesberger et al. | 623/20 |
| 4,976,740 | 12/1990 | Kleiner | 623/23 |
| 5,032,134 | 7/1991 | Lindwer | 623/23 |
| 5,147,386 | 9/1992 | Carignan et al. | 623/21 |
| 5,226,916 | 7/1993 | Goodfellow et al. | 623/20 |

FOREIGN PATENT DOCUMENTS

| | | |
|---|---|---|
| 0029787.1 | 11/1980 | European Pat. Off. . |
| 0186471 | 7/1986 | European Pat. Off. ............ 623/20 |
| 0472475 | 2/1992 | European Pat. Off. ............ 623/20 |
| 0497079 | 8/1992 | European Pat. Off. ............ 623/20 |
| 2845231 | 5/1979 | Germany . |
| 3741492 | 6/1989 | Germany ............ 623/18 |
| 0602171 | 4/1978 | U.S.S.R. . |
| 0835433 | 6/1981 | U.S.S.R. . |
| 1061811 | 12/1983 | U.S.S.R. ............ 623/20 |
| 8906946 | 8/1989 | WIPO ............ 623/18 |

*Primary Examiner*—David H. Willse
*Attorney, Agent, or Firm*—Nydegger & Associates

[57] ABSTRACT

A prosthetic knee joint to articulate and rotate the femur relative to the tibia includes an artificial femoral condyle which is mechanically attachable to the femur, and an artificial tibial plateau which is mechanically attachable to the tibia for articulation with the femoral condyle. The femoral condyle has a convex surface and a pair of cylindrical lobes which coaxially extend from the femoral condyle. On the other hand, the tibial plateau has a concave recess which slidingly receives the convex surface and it has a concave cradle which slidingly receives the pair of cylindrical lobes. For operation of the knee joint the concave recess and the concave cradle are oriented and dimensioned on the plateau to sequentially and respectively receive the convex surface and the pair of cylindrical lobes as the femur is moved in flexion and extension relative to the tibia.

19 Claims, 2 Drawing Sheets

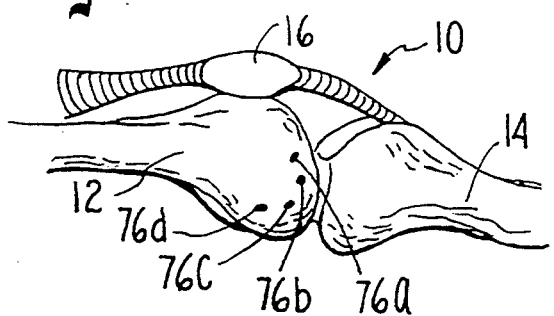
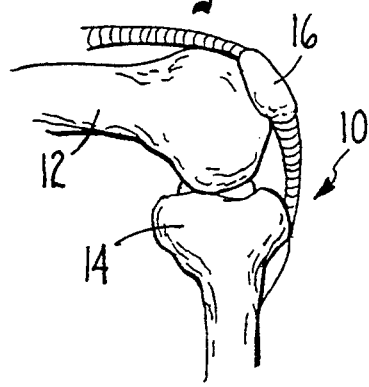
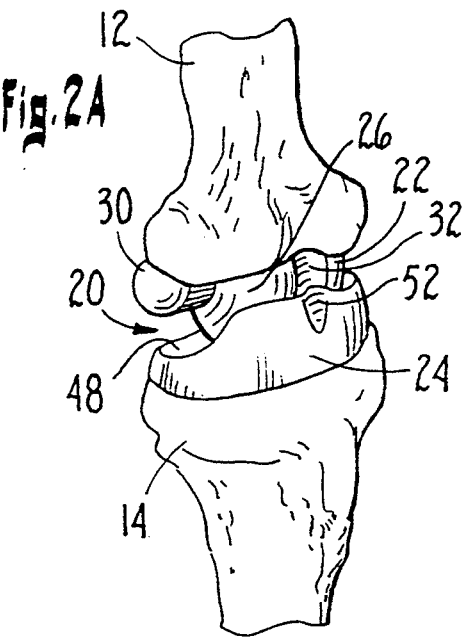
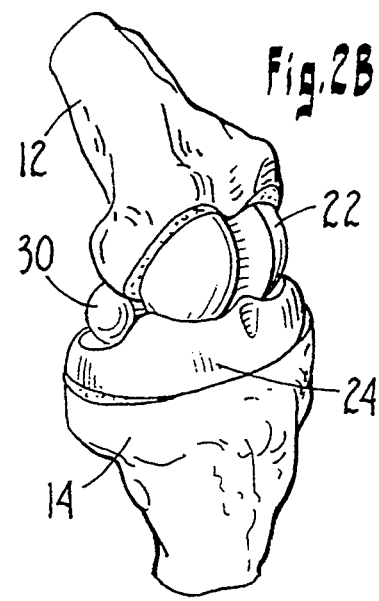
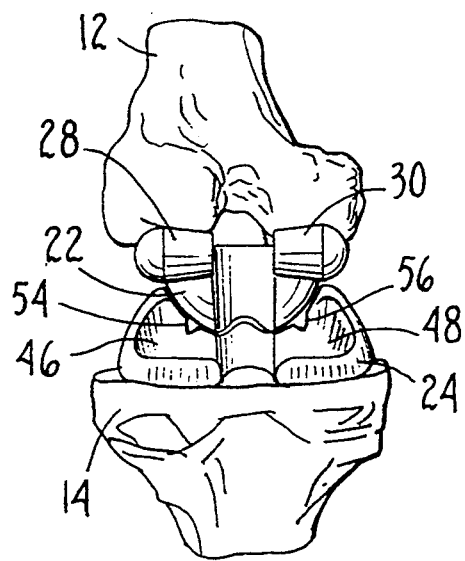
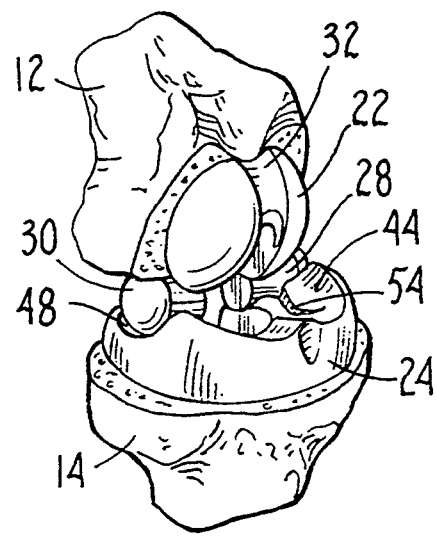

PROSTHETIC KNEE JOINT

FIELD OF THE INVENTION

The present invention pertains generally to prosthetic devices which are useful as replacement joints for limbs of the body. More specifically, the present invention pertains to prosthetic devices which can be mechanically attached to the bone. The present invention is particularly, but not exclusively, useful as a knee joint.

BACKGROUND OF THE INVENTION

For various reasons, such as a consequence of disease or injury, it is often necessary to implant a prosthetic knee joint into the leg of a patient. When doing so, it is obviously desirable to replicate the normal movement of an anatomical knee as accurately and precisely as possible. Various attempts have been made for this purpose.

Typically, whenever it has been necessary to implant a prosthetic knee joint, the accepted procedure has been to first remove a substantial amount of bone from both the distal end of the femur and from the proximal end of the tibia. A pad having a substantially flat surface is then anchored and cemented onto the proximal end of the tibia, with the flat surface exposed. A curved bearing surface is also anchored and cemented onto the distal end of the femur. During use, the curved bearing surface is then allowed to slide over the flat surface for articulation of the prosthetic joint. Unfortunately, when compared to the normal movement of an anatomical knee, with a prosthetic knee joint wherein a single curved surface articulates relative to a single substantially flat surface the resultant articulation is significantly limited. Further, although there may be some structure to limit articulation of such a prosthesis to only flexion and extension, stability problems can still develop whenever the surfaces do not effectively interlock. A prosthetic knee is particularly susceptible to this defect when one surface is substantially flat.

In addition to the purely mechanical problems which are encountered with prosthetic knee joints, there are also materials problems. More specifically, the materials which are often used in the manufacture of prosthetic knee joints have been found to sometimes be deficient in terms of biocompatability. For example, unless proper materials are used, it is possible for the body to reject the prosthesis or for the prosthesis to simply wear out. It is apparent that to overcome the wear out problem, materials which have extended longevity need to be used. Otherwise, the artificial joint must be replaced. It can also happen that the materials become ineffective for their intended purpose. For example, it is known that cement has a limited useful life for holding respective parts of the artificial joint on the femur and tibia.

Not unexpectedly, the process of securely attaching a prosthetic part to a bone can cause problems. A significant problem in this regard involves the amount of bone that must be removed in order for the body to accommodate the implanted prosthesis. Also, there is a phenomenon known as the "wave effect" which causes bone to assume a different resultant shape than originally intended. This "wave effect" results in a distorted and bulging surface, and predominantly occurs whenever an anchor pin or stake is driven into the bone.

In light of the above, it is an object of the present invention to provide a prosthetic knee joint which effectively replicates the normal anatomical movement of a knee. Another object of the present invention is to provide a prosthetic knee joint which conserves bone and uses viable tissue for reconstruction of the knee joint. Still another object of the present invention is to provide a prosthetic knee joint which provides extended longevity for the prosthesis by relying on boney ingrowth, rather than cement, for the connection of the prosthesis to the bone. Yet another object of the present invention is to provide a prosthesis which is effectively biocompatible and which reduces the autoimmune rejection phenomenon. Another object of the present invention is to provide a prosthetic knee joint which exhibits an effective stability. An object of the present invention is to also provide a prosthetic knee joint which is relatively simple to manufacture, acceptably easy to implant, and comparatively cost effective.

SUMMARY OF THE INVENTION

In accordance with the present invention, a prosthetic knee joint for allowing articulation and rotation of the femur relative to the tibia in both flexion and extension includes an artificial femoral condyle and an artificial tibial plateau. Both the femoral condyle and the tibial plateau are mechanically attachable to the femur and the tibia, respectively. Also, they are both preferably covered with a protective coating (e.g. titanium nitride, carbonate, carbide or diamond) for biocompatability purposes and to provide an adequate bearing surface. As intended for the present invention, a minimum amount of bone is removed for placement of the prothesis. Further, the existing ligaments and connective tissue of the body are saved and used, to the extent possible, to hold the artificial femoral condyle against the artificial tibial plateau during movement of the prosthetic knee joint. However, there is an inherent stability if these ligaments do not exist or have been sacrificed.

As is the case with an anatomically normal knee, it is necessary for the artificial femoral condyle of the present invention to articulate against and move relative to the artificial tibial plateau. To accomplish this function, the artificial femoral condyle for the knee joint is formed with a plurality of rounded protrusions. More specifically, the femoral condyle has a substantially convex surface which is located forward or anterior to a pair of rounded and tapered lobes. The posterior lobes extend coaxially from the condyle. The tibial plateau, on the other hand, has an anterior concave recess and a posterior concave cradle which are each dimensionally compatible with cooperative structures on the femoral condyle. As more fully described below, this compatibility allows the femoral condyle and the tibial plateau to congruently interact with each other.

For attachment of the femoral condyle to the femur, a plurality of interconnected barbed arms are implanted into the bone at the distal end of the femur. A screw is then engaged with the femoral condyle and is threadably joined to a locking nut that is attached to the barbed arms. This engagement of the screw with the nut then tightens the femoral condyle onto the distal end of the femur. Similarly, for attachment of the tibial plateau to the tibia, a plurality of interconnected barbed arms are implanted into the bone at the proximal end of the tibia. As before, a screw is engaged with the tibial plateau and is threadably joined to a nut that is attached to the barbed arms. This engagement tightens the tibial plateau onto the proximal end of the tibia.

With the artificial femoral condyle attached to the femur, and the artificial tibial plateau attached to the tibia, the two are held and maintained in sliding contact with each other by the action of existing ligaments and other connective tissue.

As intended for the present invention, the prosthetic knee allows for relative movement between the femur and tibia in both flexion and extension. Specifically, to accomplish this the anterior concave recess and the posterior concave cradle of the tibial plateau are dimensioned and positioned to articulate with the convex surface and the rounded lobes of the femoral condyle. More specifically, engagement of the convex surface with the anterior concave recess is accomplished sequentially with the engagement of the rounded lobes with the posterior concave cradle. Consequently, for a complete movement of the prosthetic knee joint between full extension and full flexion there will be a transition from one structural engagement to the other. As intended for the present invention, this structural cooperation allows for much greater flexion and more closely replicates the polycentric rotation of the tibia about the femur accomplished by a normal knee joint.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which:

FIG. 1A is a side view of an anatomical knee joint with the leg in extension;

FIG. 1B is a side view of an anatomical knee joint with the leg in flexion;

FIG. 2A is a perspective view of the prosthetic knee joint of the present invention with the leg in extension;

FIG. 2B is a perspective view of the prosthetic knee joint of the present invention with the leg shown partially bent;

FIG. 2C is a perspective view of the prosthetic knee joint of the present invention with the leg shown more substantially bent than as shown in FIG. 2B;

FIG. 2D is a rear view of the prosthetic knee joint of the present invention shown in FIG. 2A;

DESCRIPTION OF THE PREFERRED EMBODIMENTS

Figure 3A:
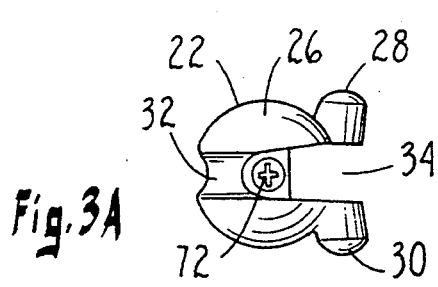
FIG. 3A is a top plan view of the femoral condyle of the present invention.

Referring initially to FIGS. 1A and 1B, an anatomical knee is shown and generally designated 10. Specifically, the knee 10 is shown to be in extension in FIG. 1A and in flexion in FIG. 1B. The more prominent anatomical components which interact with each other to establish the structure for the knee 10 are shown to include a femur 12, a tibia 14 and a patella 16. As will be appreciated by anyone skilled in the pertinent art, there are numerous connecting ligaments and other tissues which hold the femur 12 against the tibia 14 and which interact with these components and the patella 16 to move the knee 10 in a normal manner.

In FIG. 2A, a prosthetic knee joint in accordance with the present invention is shown and generally designated 20. As shown in FIGS. 2A-D, the knee joint 20 includes an artificial femoral condyle 22 and an artificial tibial plateau 24. FIGS. 2A-D also show that it is intended for the femoral condyle 22 to rest on, or articulate with, the tibial plateau 24. More specifically, it is intended for there to be a slidingly movement between the femoral condyle 22 and the tibial plateau 24 which allows the knee 20 to articulate and rotate in both flexion and extension. To cross reference the configuration of the prosthetic knee 20 with a normal knee 10, FIG. 2A (prosthetic knee 20) corresponds to FIG. 1A (normal knee 10) for extension, and FIG. 2C (prosthetic knee 20) corresponds to FIG. 1B (normal knee) for mid-range flexion. FIG. 2B for the prosthetic knee 20 is an intermediate configuration between the configurations shown in FIG. 2A and FIG. 2C.

Figure 3B:
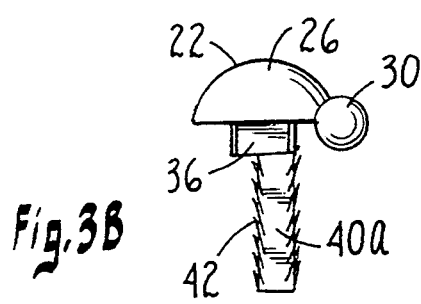
FIG. 3B is a side view of the femoral condyle of the present invention shown in FIG. 3A.
Figure 3C:
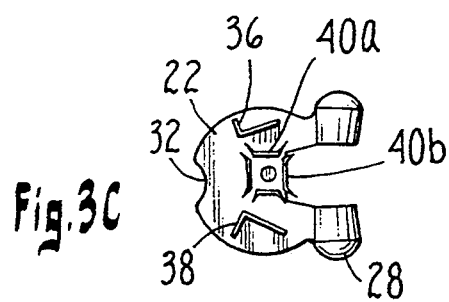
FIG. 3C is a bottom view of the femoral condyle of the present invention shown in FIG. 3A.

The structural features of femoral condyle 22 will, perhaps, be best appreciated with reference to FIGS. 3A-C. By cross referencing the FIGS. 3A-C, it can be seen that the femoral condyle 22 is formed as several rounded protrusions. Specifically, femoral condyle 22 is formed with a convex member 26 and a pair of rounded lobes 28 and 30. There is also a groove 32 which is formed into the surface of convex member 26 and there is a spacing 34 which separates the lobes 28 and 30 from each other. For reference purposes, the convex member 26 is located anteriorly on the femoral condyle 22 and the lobes 28 and 30 are located posteriorly. Further, it is to be noted that the lobes 28 and 30 are coaxially aligned for rotation about a common axis. Additionally, though both lobes 28 and 30 are substantially cylindrical, they are shown to also be tapered with diminishing diameter in a direction toward the spacing 34.

As best seen in FIGS. 3B and 3C a flange 36 and a flange 38 are attached to the underside of convex member 26 opposite from its convex surface. These Figures also show that a plurality of barbed arms 40 are attached to the femoral condyle 22 and extend therefrom in substantially the same direction as do the flanges 36 and 38. It is also to be appreciated that there are a large number of barbs 42 which are formed onto each of the barbed arms 40, and that the barbed arms specially designated 40a and 40b are only exemplary. For the present invention, in order to insure proper engagement of the barbed arms 40 with the bone, it is important that the barbs 42 are angled, as shown, toward the underside of femoral condyle 22. Additionally, to further enhance attachment to the bone, the barbs 42 are outwardly flared (see FIG. 5). As shown in the FIGS. 3B and 3C, there are four barbed arms 40 shown for femoral condyle 22. Clearly, there can be more or fewer such arms 40.

Figure 4A:
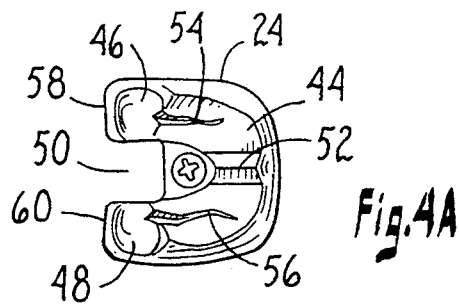
FIG. 4A is a top plan view of the tibial plateau of the present invention.
Figure 4B:
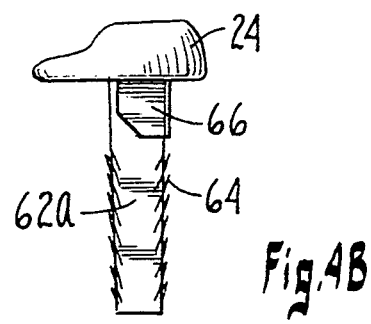
FIG. 4B is a side view of the tibial plateau of the present invention shown in FIG. 4A.
Figure 4C:
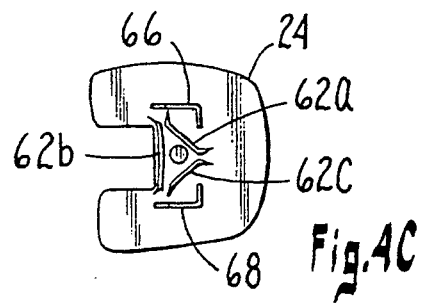
FIG. 4C is a bottom view of the tibial plateau of the present invention shown in FIG. 4A.

The structural features of tibial plateau 24 can, perhaps, be best appreciated with reference to FIGS. 4A-C. In FIG. 4A it can be seen that the tibial plateau 24 includes a concave recess 44 (see also FIG. 2C) and a pair of concave cradles 46 and 48. Like the lobes 28 and 30 of femoral condyle 22, the concave cradles 46 and 48 of tibial plateau 24 are separated from each other by a spacing 50. The tibial plateau 24 also includes a ridge 52 which protrudes from the concave recess 44 for a mating engagement with the groove 32 of femoral condyle 22. Further, the concave recess 44 is formed with a lubricating channel 54 and a lubricating channel 56 which are on opposite sides of the ridge 52.

It is to be noticed that the concave cradles 46 and 48 of tibial plateau 24, like the lobes 28 and 30 of femoral condyle, are tapered. Specifically, a lip 58 is angled relative to an edge portion of concave recess 44 to establish the tapered concave cradle 46, and a lip 60 is angled relative to an edge portion of concave recess 44 to establish the tapered concave cradle 48. As intended for the present invention of joint 20, the tapered concave cradles 46 and 48 are dimensioned to articulate with, respectively, the tapered lobe 28 and the tapered lobe 30. Also, the lips 58 and 60 are sufficiently raised to allow lobes 28 and 30 to properly center and seat into the concave cradles 46 and 48.

FIGS. 4B and 4C show that a plurality of barbed arms 62a-c extend from the underside of tibial plateau 24 and that the arms 62a-c are formed with barbs 64 which are angled, as shown, toward the underside of tibial plateau 24. Additionally, the barbs 64 are outwardly flared. In all respects, the barbed arms 62 are similar to barbed arms 40. Further, as indicated above for the barbed arms 40 of femoral condyle 22, the actual number of barbed arms 62 which are used for tibial plateau 24 is a matter of choice. Also seen extending from the underside of the tibial plateau 24 in FIGS. 4B and 4C are a flange 66 and a flange 68. Note that the flanges 66 and 68 of tibial plateau 24 are bent, as are the flanges 36 and 38 of femoral condyle 22. As can be appreciated by the skilled artisan, the extent of the bend and the orientation of the flanges 36, 38, 66 and 68 are a matter of choice. For the present invention, the configuration and orientation of the flanges 36, 38, 66 and 68 are selected to resist rotation of the femoral condyle 22 relative to the femur 12, and to resist rotation of the tibial plateau 24 relative to the tibia 14, after they are respectively affixed to the femur 12 or tibia 14.

The procedure by which the artificial femoral condyle 22 is affixed to the femur 12 is basically the same procedure which is used to affix the artificial tibial plateau 24 to the tibia. Therefore, rather than be repetitive, only the specific procedure for affixation of the femoral condyle 22 needs be discussed. This procedure will be best appreciated with reference to FIG. 5.

To begin the procedure for affixing the artificial femoral condyle 22 to the femur 12, the distal end of the femur is flattened to the extent necessary for femoral condyle 22 to snugly rest against the femur 12. Importantly, this is the only bone that is removed and, in most cases, it will be little more than a layer of bone which is approximately three millimeters thick.

After the bone surface is prepared, a shaft is chiseled or drilled into the bone for receiving each of the barbed arms 40. If there are four arms 40, then four interconnecting shafts are created which will form the outline of a rectangle. On the other hand, if there are only three arms 40, such as the three barbed arms 62 shown for tibial plateau 24, then the interconnecting shafts create the outline of a triangle. Depending on the bend and orientation of the flanges 36 and 38, compatible shafts also need to be prepared to receive these flanges 36 and 38.

Figure 5:
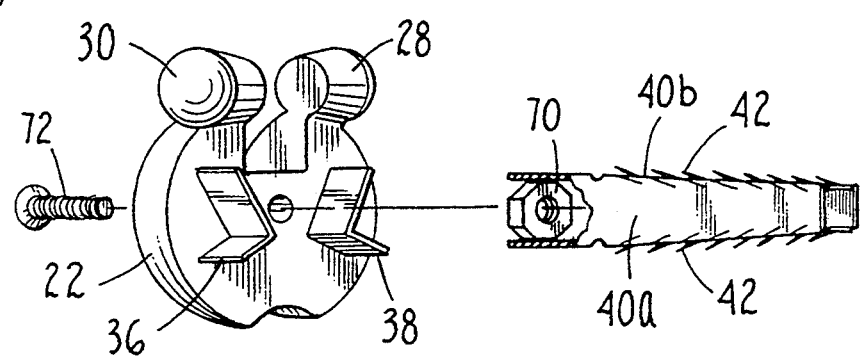
FIG. 5 is an exploded perspective view of the femoral condyle of the present invention shown with connective components for implant into the femur of a patient.

With the necessary shafts established in femur 12, the barbed arms 40 are inserted into the shafts. As indicated in FIG. 5, the plurality of arms 40 may be interconnected and, preferably, they are all fixedly attached to a nut 70. This entire structure, i.e. the plurality of barbed arms 40 and nut 70, is inserted slightly farther into the shaft than eventually desired and it is withdrawn slightly. This is done to securely seat the barbs 42 into the bone of femur 12. A screw 72 is then inserted through a hole 74 in the femoral condyle 22 for threaded engagement with the nut 70. As will be appreciated by those skilled in the pertinent art, the tightening of screw 72 onto the nut 70 will draw femoral condyle 22 toward the barbed arms 40 that were previously anchored into the femur 12. Also, the flanges 36 and 38 will be drawn into the shafts which were previously prepared to receive the flanges 36 and 38. With this operation the femoral condyle is seated onto the femur 12. As indicated above, the tibial plateau 24 is seated onto the tibia in a like manner.

Once the artificial femoral condyle 22 and the artificial tibial plateau 24 have been respectively attached to the femur 12 and tibia 14, the connecting ligaments and tissue are repositioned to assist in holding the condyle 22 against the plateau 24.

For the prosthetic knee joint 20 of the present invention, it is preferred that the component elements of the femoral condyle 22 and tibial plateau 24 be coated with a protective coating of titanium nitride or other hardened material. Additionally, it is preferable for those surfaces of the femoral condyle 22 and tibial plateau 24 which will be in intimate contact with bone tissue to be coated with a coating of hydroxylapatite. These same preferences also apply to the barbed arms 40 and 62. Further, it may be desirable if the surfaces of these components are textured to help insure a more reliable attachment between the bone tissue and the prosthesis.

The actual operation of the prosthetic knee joint 20 of the present invention will be best appreciated by referring back to FIGS. 2A, 2B and 2C. There the joint 20 is shown progressively changing in configuration from extension to flexion. It should be noted, however, that the degree of flexion shown in FIG. 2C is less than can be expected and is only exemplary. In actuality, it is envisioned that the joint 20 will make normal or near-normal flexion possible. In any event, a consideration of the change in joint 20 between extension and flexion is helpful.

When in extension, as shown in FIG. 2A, it will be seen that the convex member 26 of femoral condyle 22 is articulated with the concave recess 44 of tibial plateau 24. Also, ridge 52 is received into the groove 32 to allow rotation of the femur 12 relative to the tibia 14 consistent with the normal knee motion. Note however, that the rounded lobes 28 and 30 of the femoral condyle 22 are not in contact with tibial plateau 24 when the patient's leg is in extension.

Consider now the progression in flexion from FIG. 2A to FIG. 2C. It is known that as the tibia 14 rotates in flexion-extension relative to the femur 12, it does so about a moving center of rotation. For example, consider the representative centers 76a-d shown in FIG. 1A. This polycentric action is anatomically necessary, and is effectively duplicated by the knee joint 20 of the present invention.

For the specific change in configuration of knee joint 20 between FIG. 2A and FIG. 2B, only the convex member 26 of femoral condyle 22 is in articulation with the concave recess 44 of the tibial plateau 24. For the configuration of joint 20 attained in FIG. 2B, however, the lobes 28 and 30 of femoral condyle 22 are also in contact with the concave cradles 46 and 48 of the tibial plateau 24. Further movement of the joint 20 in flexion, as indicated by its change in configuration between FIG. 2B and FIG. 2C, causes the convex member 26 of femoral condyle 22 to lift away from the concave recess 44 of tibial plateau 24 as it does in nature. The transitional changes in configuration of the knee joint 20 is thereafter accomplished with the lobes 28 and 30 in sliding rotational contact with the concave cradles 46 and 48 of tibial plateau 24.

For a transition from flexion toward extension, the changes in configuration for joint 20 occur in the reverse order from that discussed above. In either case, i.e. either extension or flexion, the appropriate dimensioning of both femoral condyle 22 and tibial plateau 24 allows these components to mate and move relative to each other in a polycentric rotation of tibia 14 relative to femur 12. The result is a duplication of normal anatomical movement.

While the particular prosthetic knee joint as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A prosthetic knee joint for allowing articulation and rotation of the femur relative to the tibia in both flexion and extension, which comprises:
    an artificial femoral condyle attachable to the femur;
    a first rounded protrusion formed on an anterior portion of said condyle;
    a second rounded protrusion formed on a posterior portion of said condyle;
    a third rounded protrusion formed on a posterior portion of said condyle;
    an artificial tibial plateau articulated with said femoral condyle, said tibial plateau being attachable to the tibia;
    a first rounded recess formed on an anterior portion of said plateau;
    a second rounded recess formed on a posterior portion of said plateau; and
    a third rounded recess formed on a posterior portion of said plateau;
    wherein said first rounded recess, said second rounded recess, and said third rounded recess are oriented and dimensioned on said tibial plateau to sequentially receive said first rounded protrusion, said second rounded protrusion, and said third rounded protrusion, respectively, in a polycentric transition as the femur is moved in flexion or extension relative to the tibia.

2. A knee joint as recited in claim 1 wherein said first rounded protrusion comprises a first member formed with a convex surface, and said second and third rounded protrusions comprise a pair of substantially cylindrical rounded lobes attached to said first member and coaxially extending therefrom.

3. A knee joint as recited in claim 2 wherein said first rounded recess comprises a concave recess to receive said convex surface of said first member of said femoral condyle, and said second and third rounded recesses comprise a concave cradle to receive said pair of lobes of said femoral condyle.

4. A joint as recited in claim 3 wherein said concave recess of said tibial plateau is formed with a ridge, and said convex surface of said femoral condyle is formed with a groove, said ridge being received in said groove when said convex surface slidingly engages with said concave recess to maintain relative polycentric transitional movement between the tibia and the femur in flexion and extension.

5. A knee joint as recited in claim 1 further comprising a plurality of barbed arms extending from said femoral condyle and a plurality of barbed arms extending from said tibial plateau, said barbed arms extending from said femoral condyle being implantable into the femur to mechanically attach said femoral condyle to the femur, and said barbed arms extending from said tibial plateau being implantable into the tibia to mechanically attach said tibial plateau to the tibia.

6. A knee joint as recited in claim 1 further comprising a plurality of flanges extending from said femoral condyle and a plurality of flanges extending from said tibial plateau, said flanges extending from said femoral condyle being implantable into the femur to mechanically anchor said femoral condyle to the femur, and said flanges extending from said tibial plateau being implantable into the tibia to mechanically anchor said tibial plateau to the tibia.

7. A knee joint as recited in claim 1 further comprising a protective coating of titanium nitride.

8. A prosthetic joint for moving a limb in flexion and extension which comprises:
    a first member formed with a spherical convex surface;
    a pair of substantially cylindrical tapered lobes attached to said first member and coaxially extending therefrom, said tapered lobes each having a spherical convex end; and
    a second member formed with a rounded concave recess to receive said convex surface of said first member for engagement of said first member with said second member, and said second member being further formed with a rounded concave cradle to receive said pair of lobes for engagement of said lobes with said second member, said concave recess and said concave cradle configured to sequentially receive said spherical convex surface and said rounded lobes, respectively, in a polycentric transitional movement between articulated members of said limb during flexion and extension.

9. A joint as recited in claim 8 wherein said joint is a prosthesis for the knee to allow articulation and rotation of the femur relative to the tibia in flexion and extension, and wherein said first member and said pair of substantially cylindrical lobes form an artificial femoral condyle mechanically attachable to the femur.

10. A joint as recited in claim 9 wherein said second member is an artificial tibial plateau, said artificial tibial plateau being mechanically attachable to the tibia for sliding engagement with said artificial femoral condyle.

11. A joint as recited in claim 10 wherein said concave recess and said concave cradle are oriented and dimensioned on said plateau to sequentially and respectively receive said convex surface and said pair of rounded lobes as the femur is moved in flexion and extension relative to the tibia.

12. A joint as recited in claim 10 wherein said concave recess of said tibial plateau is formed with a ridge, and said convex surface of said femoral condyle is formed with a groove, said ridge being received in said groove when said convex surface slidingly engages with said concave recess to maintain relative movement between the tibia and the femur in flexion and extension.

13. A joint as recited in claim 10 further comprising a plurality of barbed arms extending from said femoral condyle and a plurality of barbed arms extending from said tibial plateau, said barbed arms extending from said femoral condyle being implantable into the femur to attach said femoral condyle to the femur, and said barbed arms extending from said tibial plateau being implantable into the tibia to attach said tibial plateau to the tibia.

14. A joint as recited in claim 10 further comprising a plurality of flanges extending from said femoral condyle and a plurality of flanges extending from said tibial plateau, said flanges extending from said femoral condyle being implantable into the femur to anchor said femoral condyle to the femur, and said flanges extending from said tibial plateau being implantable into the tibia to anchor said tibial plateau to the tibia.

15. A joint as recited in claim 8 further comprising a protective coating of titanium nitride.

16. A method for establishing a prosthetic knee joint using an artificial femoral condyle and an artificial tibial plateau to allow articulation and rotation of the femur relative to the tibia in flexion and extension, the artificial femoral condyle having a spherical convex surface and a pair of tapered substantially cylindrical rounded lobes attached thereto, and the artificial tibial plateau having a rounded concave recess and a rounded concave cradle, the concave recess being used for receiving the convex surface and the concave cradle being used for receiving the rounded lobes in a polycentric transitional movement between the tibia and the femur during flexion and extension, which comprises the steps of:

creating a plurality of shafts into the distal end of the femur;
creating a plurality of shafts into the proximal end of the tibia;
driving a plurality of barbed arms into the femur by placing one said barbed arm into each of the shafts in the femur;
driving a plurality of barbed arms into the tibia by placing one said barbed arm into each of the shafts in the tibia;
attaching the artificial femoral condyle to the barbed arms in the femur; and
attaching the artificial tibial plateau to the barbed arms in the tibia to position the plateau to receive the condyle for said polycentric transitional movement.

17. A method as recited in claim 16 further comprising the step of withdrawing said barbed arms a predetermined distance after said barbed arms are driven into the shafts to attach said barbed arms respectively to the femur and the tibia.

18. A method as recited in claim 16 wherein said plurality of barbed arms attachable to the femoral condyle are fixedly connected to a nut, and a screw is engaged with the femoral condyle and threadably joined to the locking nut to attach the femoral condyle to the barbed arms, and wherein said plurality of barbed arms attachable to the tibial plateau are fixedly connected to a nut, and a screw is engaged with the tibial plateau and threadably joined to the nut to attach the tibial plateau to the barbed arms.

19. A method as recited in claim 16 further comprising the step of lubricating said joint by forming lubrication channels on said tibial plateau to channel fluid between said condyle and said plateau upon articulation of said joint.

* * * * *